United States Patent [19]

Seemuth

[11] 4,317,934

[45] Mar. 2, 1982

[54] PREPARATION OF CARBONYL COMPOUNDS

[75] Inventor: Paul D. Seemuth, Oak Park, Mich.

[73] Assignee: Ethyl Corporation, Richmond, Va.

[21] Appl. No.: 178,460

[22] Filed: Aug. 15, 1980

[51] Int. Cl.[3] .................... C07C 45/28; C07C 45/43
[52] U.S. Cl. .................................................. 568/437
[58] Field of Search ...................... 568/437, 426, 700

[56] References Cited

FOREIGN PATENT DOCUMENTS 20909 3/1882 Fed. Rep. of Germany ...... 568/437

OTHER PUBLICATIONS

Harfenist et al, The Jour. of Org. Chem., (1954), vol. 19, pp. 1608–1616.
Karrer, Org. Chem., (1950), pp. 450–451.
Weygand/Hilgetag, Preparative Org. Chem., (1972), pp. 336–337.

*Primary Examiner*—Bernard Helfin
*Attorney, Agent, or Firm*—Donald L. Johnson; Joseph D. Odenweller; John F. Hunt

[57] ABSTRACT

Process for preparing an aldehyde by hydrolysis of a monohalide and a dihalide, thereby obtaining a mixture of an alcohol and an aldehyde, and further reacting said mixture with manganese dioxide to convert said alcohol to said aldehyde.

8 Claims, No Drawings

PREPARATION OF CARBONYL COMPOUNDS

BACKGROUND OF THE INVENTION

Aldehydes or ketones, hereinafter collectively referred to as aldehydes, are conventionally made by hydrolysis of geminal dihalides. In the preparation of geminal dihalides, the monohalo derivative is often a contaminant. Since the monohalo and dihalo species can be difficult to separate, hydrolysis to the aldehyde and alcohol from the crude geminal dihalide is normally done followed by a separation procedure to remove the alcohol. This separation procedure can be both time-consuming and economically impractical. Through the use of manganese dioxide this procedure may be eliminated. This process stops upon conversion to the desired aldehyde and does not continue beyond this to formation of the acid.

Use of manganese dioxide as an oxidizing agent for alcohols has been reported in a 1976 review article in Synthesis entitled "Active Manganese Dioxide Oxidation in Organic Chemistry," by Alexander J. Fatiadi, pages 65 through 104 and 133 through 167.

SUMMARY OF THE INVENTION

In accordance with the present invention, a greater yield of aldehyde can be obtained from the hydrolysis of a crude mixture of monohalides and geminal dihalides by further reacting said mixture with manganese dioxide, thereby converting the alcohol produced to aldehyde while the aldehyde formed upon the initial hydrolysis remains unaffected.

DESCRIPTION OF THE PREFERRED EMBODIMENTS

A preferred embodiment for this invention is an improvement in a process for selectively producing an aldehyde or ketone by a process which comprises hydrolyzing a geminal dihalide containing a monohalide impurity to form a mixture of an aldehyde and an alcohol, the improvement comprising further reacting said mixture with manganese dioxide to convert said alcohol to additional aldehyde, thereby eliminating the need for a separation procedure to remove said alcohol.

The geminal dihalides include all organic compounds which have two halogen atoms bonded to a single carbon atom. These compounds can be exemplified by dihaloalkanes containing from 1 to about 20 carbon atoms, dihaloalkenes containing from 2 to about 20 carbon atoms and α,α-dihalotoluenes containing from 7 to about 20 carbon atoms.

The dihaloalkanes can be represented by the formula:

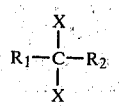

wherein $R_1$ and $R_2$ are selected from the group consisting of hydrogen and alkyl groups containing from 1 to about 19 carbon atoms. More preferably $R_1$ is hydrogen and $R_2$ is an alkyl containing 1 to 19 carbon atoms. The dihaloalkanes include compounds such as methylene chloride, 1,1-dichloroethane, 1,1-dichlorononane, 2,2-dibromoundecane, 1,1-dichloroeicosane, 4,4-dibromoeicosane and the like.

The dihaloalkenes can be represented by the formula:

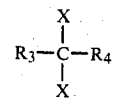

wherein $R_3$ and $R_4$ are selected from the group consisting of hydrogen, alkyl groups containing 1 to about 17 carbon atoms and alkenyl groups containing 2 to about 19 carbon atoms, wherein at least one of $R_3$ and $R_4$ represents an alkenyl group. More preferably $R_3$ is an alkenyl group containing 2 to about 19 carbon atoms and $R_4$ is hydrogen. The dihaloalkenes include compounds such as 1,1-dichloro-2-butene, 1,1-dibromo-2-propene, 2,2-dichloro-4-octene, 1,1-dibromo-2-tridecene, 1,1-dichloro-9-eicosene and the like.

The geminal dihalides are represented by X in the foregoing examples. These halides attached to the same carbon atom can be selected from the group consisting of chlorine, bromine and iodine. A more preferred halide is chlorine.

A further preferred embodiment of this invention involves hydrolyzing an α,α-dihalotoluene having the structure:

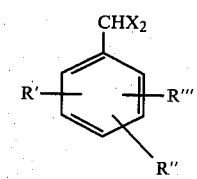

wherein R', R" and R''' are selected from the group consisting of hydrogen, halide, alkyl containing from 1 to about 20 carbon atoms, cycloalkyl containing from 5 to 8 carbon atoms, aralkyl containing from 7 to about 20 carbon atoms, aryl containing from 6 to about 20 carbon atoms, alkoxy containing from 6 to about 20 carbon atoms and aryloxy containing from 6 to about 20 carbon atoms.

The halogens represented by R', R" and R''' include chlorine, bromine and iodine. The more preferred halogens are chlorine and bromine.

X also represents a halogen. These halogens include chlorine, bromine and iodine. A more preferred halogen is chlorine.

The α,α-dihalotoluenes include compounds such as α,α-dibromotoluene, α,α-dichloro-4-methyltoluene, α,α-2,4-tetrachlorotoluene, α,α-dichloro-3-phenoxytoluene, α,α-dichloro-4-sec-tridecyltoluene, α,α-dibromo-4-methoxytoluene, α,α-dichloro-4-cyclohexyltoluene, 4-(α-methylbenzyl)-α,α-dibromotoluene, 4-(dichloromethyl)biphenyl and the like. Other miscellaneous geminal dihalides include 1,1-dibromocyclohexane, 1-dichloromethylnaphthalene, α,α-dibromo-4-nitrotoluene, 2-dichloromethylbenzophenone and the like.

The monohalide impurity present in the reaction mixture has a structure identical to the structure of the geminal dihalide, except a hydrogen is substituted for one of the geminal halides. The monohalo derivatives can be exemplified by haloalkanes containing from 1 to about 20 carbon atoms, haloalkenes containing from 2 to about 20 carbon atoms and α-halotoluenes containing from 7 to about 20 carbon atoms.

The haloalkanes include compounds such as methyl chloride, 1-chloroeicosane and the like. The haloalkenes include compounds such as allyl chloride, 1-bromo-9-eicosene and the like. The α-halotoluenes include α-bromotoluene, α2,4-trichlorotoluene, α-chloro-3-phenoxytoluene and the like.

Hydrolysis of the mixture of geminal dihalide and monohalide yields aldehydes or ketones and alcohols. The geminal dihalide component which can be represented by the structure:

is converted to the aldehyde or ketone, hereinafter referred to as aldehyde, having the structure $>C=O$. The monohalide impurity which can be represented by the structure:

is converted to the alcohol having the structure:

The geminal dihalide, monohalide, aldehyde and alcohol represented by the above structures each contain a carbon atom. The unspecified substituents attached to said carbon atom are identical in each of the above categories.

The hydrolysis of the geminal dihalide and monohalide to the corresponding aldehyde and alcohol can be done by a variety of known methods. A mixture of the monohalide and dihalide may be combined with water and a base in an autoclave. A minimum of one mole of water and a minimum of two equivalents of any organic base per mole of dihalide is necessary. Common examples of bases include $NaHCO_3$, $Na_2CO_3$, NaOH, KOH and the like. The base is designed to neutralize the acid produced during this process, thereby driving the reaction to completion.

This combination of ingredients may be refluxed at atmospheric pressure and the temperature ranges from room temperature to 100° C. However, a higher pressure permits higher temperature to be achieved, thus shortening the reaction time. The pressure generally ranges from about 15 psig to about 7500 psig. The corresponding temperature extends from room temperature to about 250° C. The choice of reaction conditions is dependent upon the stability of the final products.

Once the hydrolysis is complete, the product is removed and the organic and aqueous layers are separated. The product is washed with water and dried. Common drying agents include $Na_2SO_4$ and $MgSO_4$.

Manganese dioxide, $MnO_2$, is now added to this aldehyde/alcohol mixture to substantially remove the alcohol impurity and thus obtain an increased yield of aldehyde.

A minimum of one mole of $MnO_2$ per mole of alcohol is necessary for this oxidation. Crude $MnO_2$ as the natural ore appears to be as effective as active $MnO_2$, but reaction time can be reduced considerably through the use of active $MnO_2$. Several methods are available to produce active $MnO_2$. One commonly used method is described by Attenburrow in his article "A Synthesis of Vitamin A from Cyclohexanone," in *Journal of the Chemical Society* (1952), page 1104, incorporated herein by reference.

An organic solvent may be added in addition to the manganese dioxide. Possible solvents include chloroform, dioxane, ethers and the like. The most frequently used organic solvent in this type of oxidation is diethyl ether. The amount of ether that may be added varies considerably, but it is generally in the range of 1-50 ml of ether per gram of mixture.

The $MnO_2$ reaction may be conducted at pressures up to 1000 psig or more. This is controlled by temperature and vapor pressure. Since this reaction occurs on a solid surface, it is preferably run at atmospheric pressure.

The $MnO_2$ reaction is conducted at a temperature high enough to allow the oxidation to proceed at a reasonable rate, yet not so high as to cause decomposition of reactants or products. A preferred temperature range is from about 30° C. to 300° C. A more preferred temperature range is from 50° C. to 200° C. The maximum temperature is dependent upon the boiling point of the respective solvent.

In addition to temperature and pressure, reaction time is dependent upon the activity of the $MnO_2$. If active $MnO_2$ is used, a significant improvement in aldehyde yield is obtained within two to three hours. The following example illustrates the way the process is carried out.

EXAMPLE

To a 600 cc Hastoloy C autoclave was charged 48.52 g of a crude chlorination mixture containing 10.93% 2,4-dichlorotoluene, 70.39% α,2,4-trichlorotoluene, 18.52% α,α,2,4-tetrachlorotoluene, 0.10% α,α,2,4-pentachlorotoluene (the percentages represent gas chromatograph area percents), 39 g of sodium bicarbonate and 146 ml of water. The autoclave was flushed with nitrogen and pressure tested to 1500 psig. The autoclave was then vented to atmospheric pressure and heated. The temperature was increased to 160° C. and maintained for two hours. The pressure increased from atmosphere pressure to between 200 and 400 psig. After two hours, the autoclave was cooled to 80° C., vented and the product removed. After separation of the aqueous phase, the crude aldehyde mixture was flash distilled affording 11.84% 2,4-dichlorotoluene, 16.94% 2,4-dichlorobenzaldehyde and 71.21% 2,4-dichlorobenzyl alcohol.

To 0.4 g of this toluene-benzaldehyde-alcohol mixture was added 20 ml of diethyl ether and 0.98 g of $MnO_2$ prepared by Attenburrow's method. The mixture was stirred for two hours at room temperature, filtered to remove the $MnO_2$ and analyzed for aldehyde-alcohol concentrations. Gas chromatographic analysis on a 10' 10% SE-30 column indicated a 48% decrease in alcohol concentration after two hours, a 55% decrease after six hours and a 63% decrease after 72 hours.

The invention is not limited to the foregoing description. A wide variety of starting materials may be used. For instance, α,α-dichloro-3-phenoxytoluene can be substituted for α,α,2,4-tetrachlorotoluene to obtain 3-phenoxybenzaldehyde and α-chloro-3-phenoxytoluene can be substituted for α,2,4-trichlorotoluene to obtain 3-phenoxybenzyl alcohol by the first hydrolysis step and 3-phenoxybenzaldehyde by the later oxidation step.

A variety of aldehydes can be produced by this invention. These aldehydes are useful as pesticide intermediates, drug intermediates or in the production of plasticizers.

I claim:

1. In a process for selectively producing an aldehyde by a procedure which comprises hydrolyzing a geminal dihalide containing a monohalide impurity to form a mixture of an aldehyde and an alcohol, the improvement comprising further reacting said mixture with manganese dioxide to convert said alcohol to additional aldehyde thereby eliminating the need for a separation procedure to remove said alcohol.

2. A process of claim 1 wherein the halide on the geminal dihalide and monohalide molecule is selected from the group consisting of chlorine, bromine and iodine.

3. A process of claim 2 wherein said halide is chlorine.

4. A process of claim 1 whereby said geminal dihalide is an α,α-dihalotoluene having the structure:

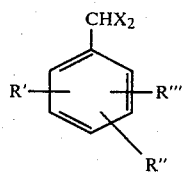

wherein R', R" and R'" are selected from the group consisting of hydrogen, halide, alkyl containing from 1 to 20 carbon atoms, cycloalkyl containing from 5 to 8 carbon atoms, aralkyl containing from 7 to 20 carbon atoms, aryl containing from 6 to 20 carbon atoms, alkoxy containing from 6 to 20 carbon atoms, aryloxy containing from 6 to 20 carbon atoms and X is a halogen, and said monohalide is an α-halotoluene having the structure:

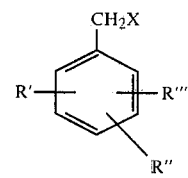

wherein R', R", R'" and X are the same as those attached to said α,α-dihalotoluene.

5. A process of claim 4 wherein the halide on the geminal dihalide and monohalide molecule is selected from the group consisting of chlorine, bromine and iodine.

6. A process of claim 5 wherein said halide is chlorine.

7. A process of claim 4 wherein said α,α-dihalotoluene is α,α,2,4-tetrachlorotoluene and said α-halotoluene is α,2,4-trichlorotoluene.

8. A process of claim 4 wherein said α,α-dihalotoluene is α,α-dichloro-3-phenoxytoluene and said α-halotoluene is α-chloro-3-phenoxytoluene.

* * * * *